United States Patent [19]

Hughes

[11] 4,066,705

[45] Jan. 3, 1978

[54] POLYBENZIMIDAZOLE FIBER SUPPORTED CATALYST

[75] Inventor: O. Richard Hughes, Chatham, N.J.

[73] Assignee: Celanese Corporation, New York, N.Y.

[21] Appl. No.: 624,798

[22] Filed: Oct. 22, 1975

[51] Int. Cl.$^2$ ............................................. C07C 45/08
[52] U.S. Cl. ............................ 260/604 HF; 252/428; 252/449
[58] Field of Search ............. 260/604 HF; 252/449 R

[56] References Cited

U.S. PATENT DOCUMENTS

| | | | |
|---|---|---|---|
| 3,594,425 | 7/1971 | Brader | 260/604 HF |
| 3,636,159 | 1/1972 | Solomon | 260/604 HF |

*Primary Examiner*—James O. Thomas, Jr.
*Assistant Examiner*—W. B. Lone

[57] ABSTRACT

An improved catalyst is provided which is useful in hydroformylation reactions comprising a rhodium carbonyl complex and a polybenzimidazole fiber support wherein under hydroformylation conditions the rhodium carbonyl complex forms a catalytically active polybenzimidazole complex with the benzimidazole units of the polybenzimidazole fiber surface acting as donor ligands for the rhodium carbonyl complex. This fiber supported catalyst may be readily separated from the products of the hydroformylation reaction by simple filtration.

4 Claims, No Drawings

POLYBENZIMIDAZOLE FIBER SUPPORTED CATALYST

BACKGROUND OF THE INVENTION

It is well known that various olefins can be reacted with carbon monoxide and hydrogen so as to be converted into corresponding aldehydes and/or alcohols. These reactions are often referred to as oxo or hydroformylation reactions. It is also well known that such hydroformylation reactions are catalyzed by a select group of catalytic systems which include the metals of rhodium, ruthenium, rhenium cobalt, platinum, palladium, osmium, and iridium. However, catalysts containing such valuable nobel metals must be recovered from the products of reaction and recycled to the reaction zone. Such recovery is a relatively expensive operation and greatly increases the costs of the process. Insolubilized catalysts, such as the one disclosed herein, can be separated from reaction products by simple filtration. A preferred embodiment for effecting catalyst separation includes utilizing the supported catalyst in the form of screens, webs, cloths, etc. which can easily be loaded and/or unloaded into or from a commercial reactor. This is an improvement over other catalyst supports utilized in the past which have generally taken the form of polymer beads, gels, inorganic beads, spheres, cylinders, irregular granules, etc. which may require careful loading to avoid uneven pressure drops due to uneven pellet distribution, or to build up of fines from crushed pellets, etc.

Additionally, the ability of polybenzimidazole to form a stable insoluble complex with rhodium carbonyl chloride may be utilized to achieve recovery of the rhodium metal from solution.

It is an object of the present invention to provide an improved hydroformylation process which utilizes a polybenzimidazole (PBI) fiber supported rhodium carbonyl complex.

It is another object of the present invention to provide an improved catalytic system to be utilized in hydroformylation reactions which may be readily separated from the reaction products and reused repeatedly.

It is a further object of the present invention to provide a method of making a polybenzimidazole fiber supported rhodium carbonyl complex to be utilized in hydroformylation reactions.

It is a further object of the present invention to provide a method of making a supported catalyst that can be fabricated in the form of screens, cloths, webs, and hollow tubes.

It is still a further object of the present invention to provide a means for recovering rhodium metal from solution.

These and other objects, as well as the scope, nature, and utilization of the invention, will be apparent to those skilled in the art from the following description and appended claims.

SUMMARY OF THE INVENTION

In one aspect, the present invention provides for an improved catalyst useful in hydroformylation reactions comprising a rhodium carbonyl complex of the type $[Rh(CO)_nX_y]_2{}^a$, where (a) may vary from 0 to $-2$, $n$ may vary from 1 to 2, $y$ may vary from 1 to 2 and X is a member selected from one group consisting essentially of halogen, carboxylate, nitrate, thiocyanate, and sulfate, and a polybenzimidazole fiber support wherein said rhodium carbonyl complex forms a polybenzimidazole complex with the benzimidazole units of the polybenzimidazole fiber surface thereby acting as donor ligands for the rhodium carbonyl complex. The rhodium carbonyls on the surface of the polybenzimidazole fiber are coordinately bonded to the benzimidazole structures of the surface of the fiber.

In another aspect, the present invention provides for a hydroformylation process in which an olefinic material is reacted with carbon monoxide and hydrogen under hydroformylation conditions; the improvement of which comprises carrying out the reaction in the presence of a polybenzimidazole fiber-supported rhodium catalyst.

In still another aspect, the present invention provides for a process for making a polybenzimidazole fiber-supported rhodium catalyst which comprises; forming a rhodium carbonyl complex of that type described above and reacting said complex with a polybenzimidazole fiber wherein the benzimidazole units of the polybenzimidazole fiber surface act as donor ligands of the rhodium carbonyl complex.

The present invention represents an enormous simplification in the product separation steps usually associated with hydroformylation reactions of the prior art. Thus the value of the supporting rhodium carbonyls on polybenzimidazole fibers is that the products of a reaction catalyzed by the insoluble catalyst can be separated from the catalyst by simple filtration. This eliminates any possibility of catalyst decomposition as a result of the conditions of product separation imposed by the prior art.

DESCRIPTION OF THE PREFERRED EMBODIMENTS

Polybenzimidazoles are a known class of heterocyclic polymers which consist essentially of recurring units of the following formulas I and II. Formula I is:

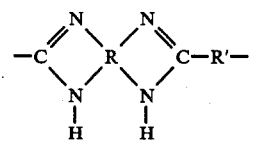

wherein R is a tetravalent aromatic nucleus, with the nitrogen atoms forming the benzimidazole rings being paired upon adjacent carbon atoms, i.e., ortho carbon atoms, of the aromatic nucleus and R' is a member of the class consisting of an aliphatic (alkylene) group, preferably having 4 to 8 carbon atoms, a cycloaliphatic ring, an aromatic ring and a heterocyclic ring such as pyridine, pyrazine, furan, quinoline, thiophene, and pyran. Formula II is:

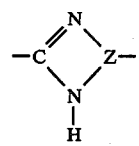

wherein Z is an aromatic nucleus having the nitrogen atoms forming the benzimidazole ring paired upon adjacent carbon atoms of the aromatic nucleus.

Preferably, the continuous filamentary materials are prepared from aromatic polybenzimidazoles, that is, from polymers consisting essentially of the recurring units of Formula I wherein R' is an aromatic ring or a heterocyclic ring.

As set forth in the U.S. Pat. No. 3,174,947 and Re. Pat. No. 26,065, which are incorporated herein by reference, the aromatic polybenzimidazoles having the recurring units of Formula II may be prepared by self-condensing a trifunctional aromatic compound containing only a single set of ortho-disposed diamino substituents and an aromatic, preferably phenyl, carboxylate ester substituent. Exemplary of polymers of this type is poly-2,5(6)-benzimidazole prepared by the autocondensation of phenyl-3,4-diamonobenzoate.

As also set forth in the above-mentioned patent, the aromatic polybenzimidazoles having the recurring units of Formula I may be prepared by condensing an aromatic tetraamine compound containing a pair of orthodiamino substituents on the aromatic nucleus with a dicarboxyl compound selected from the class consisting of (a) the diphenyl ester of an aromatic dicarboxylic acid, (b) the diphenyl ester of a heterocyclic dicarboxylic acid wherein the carboxyl groups are substituents upon a carbon in a ring compound selected from the class consisting of pyridine, pyrazine, furan, quinoline, thiophene and pyran and (c) an anhydride of an aromatic dicarboxylic acid.

Examples of polybenzimidazoles which have the recurring structure of Formula I are as follows:

poly-2,2'(b-phenylene)5,5'-bibenzimidazole;
poly-2,2'-(pyridylene-3",5")-5,5'-bibenzimidazole;
poly-2,2'-(furylene-2",5")-5,5'-bibenzimidazole;
poly-2,2'-(naphthalene-1",6")-5,5'-bibenzimidazole;
poly-2,2'-(biphenylene-4",4")-5,5'-bibenzimidazole;
poly-2,2'-amylene-5,5'-bibenzimidazole;
poly-2,2'-octamethylene-5,5'-bibenzimidazole;
poly-2,6-(m-phenylene)-diimidazobenzene;
poly-2,2'-cyclohexeneyl-5,5'-bibenzimidazole;
poly-2,2'(m-phenylene)-5,5'-di(benzimidazole) ether;
poly-2,2'(m-phenylene)-5,5'-di(benzimidazole) sulfide;
poly-2,2'(m-phenylene)-5,5'-di(benzimidazole) sulfone;
poly-2,2'(m-phenylene)-5,5'-di(benzimidazole) methane
poly-2'2"(m-phenylene)-5'5" di(benzimidazole) propane-2,2; and
poly-2',2"(m-phenylene)-5',5" di(benzimidazole) ethylene-1,2 where the double bonds of the ethylene groups are intact in the final polymer.

The preferred polybenzimidazole for use in the present process is one prepared from poly-2,2'-(m-phenylene)5,5'-bibenzimidazole the recurring unit of which is:

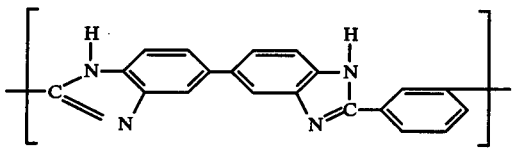

Any polymerization process known to those skilled in the art may be employed to prepare the polybenzimidazole which may then be formed into a continuous length of fibrous material. Representative techniques for preparing the polybenzimidazole are disclosed in U.S. Pat. Nos. 3,509,108, 3,549,603, and 3,551,389, which are assigned to the assignee of the present invention and are herein incorporated by reference.

With respect to aromatic polybenzimidazoles, preferably equimolar quantities of the monomeric tetramine and dicarboxyl compound are introduced into a first stage melt polymerization reaction zone and heated therein at a temperature above about 200° C., preferably at least 250° C., and more preferably from about 270° to 300° C. The reaction is conducted in a substantially oxygen-free atmosphere, i.e., having below about 20 ppm oxygen, until a foamed prepolymer is formed having an intrinsic viscosity, expressed as deciliters per gram, of at least 0.1, and preferably from about 0.13 to 0.3, the inherent viscosity (I.V.) as used herein being determined from a solution of 0.4 grams of the polymer in 100 ml. of 97% $H_2SO_4$ at 25° C.

After the conclusion of the first stage reaction, which normally takes at least 0.5 hour and preferably 1 to 3 hours, the foamed prepolymer is cooled and then powdered or pulverized in any convenient manner. The resulting prepolymer powder is then introduced into a second stage polymerization reaction zone wherein it is heated under substantially oxygen-free conditions, as described above, to yield a polybenzimidazole polymer product, desirably having an I.V., as measured above, of at least 0.6, e.g., 0.80 to 1.1 or more.

The temperature employed in the second state is at least 250° C., preferably at least 325° C., and more preferably from about 350° to 425° C. The second stage reaction generally takes at least 0.5 hour, and preferably from about 1 to 4 hours or more.

A particularly preferred method for preparing the polybenzimidazole is disclosed in the aforesaid U.S. Pat. No. 3,509,108. As disclosed therein aromatic polybenzimidazoles may be prepared by initially reacting the monomer in a melt phase polymerization at a temperature above about 200° C. and a pressure above 50 p.s.i. (e.g., 300 to 600 p.s.i) and then heating the resulting reaction product in a solid state polymerization at a temperature above about 300° C. (e.g., 350° to 500° C.) to yield the final product.

Preparation of the Continuous Length of Fibrous Material

The term "continuous length of polybenzimidazole fibrous material" as used herein includes monofilaments, as well as multifilament fibrous materials, such as yarn, strand cable tow and the like. In a preferred embodiment of the process the continuous length of polybenzimidazole fibrous material is a multifilament yarn or a multifilament tow.

As is known in the art, polybenzimidazoles are generally formed into continuous lengths of fibrous materials by solution spinning, that is, by dry or wet spinning a solution of the polymer in an appropriate solvent such as N,N-dimethylacetamide, N,N-dimethylformamide, dimethylsulfoxide or sulfuric acid (used only in wet spinning) through an opening of predetermined shape into an evaporative atmosphere for the solvent in which most of the solvent is evaporated (dry) or into a coagulation bath (wet), resulting in the polymer having the desired filamentary shape.

The polymer solution may be prepared in accordance with known procedures. For example, sufficient polybenzimidazole may be dissolved in the solvent to yield a final solution suitable for extrusion containing from about 10 to 45% by weight of the polymer, based on the total weight of the solution, preferably from about 20 to 30% by weight.

One suitable means for dissolving the polymer in the solvent is by mixing the materials at a temperature above the atmospheric boiling point of the solvent, for example 25° to 120° C. above such boiling point, and at a pressure of 2 to 15 atmospheres for a period of 1 to 5 hours.

Preferably, the polymer solutions, after suitable filtration to remove any undissolved portions, are dry spun. For example, the solutions may be extruded through a spinneret into a conventional type downdraft spinning column containing a circulating inert gas such as nitrogen, noble gases, combustion gases or superheated steam. Conveniently, the spinneret face is at a temperature of from about 100° to 170° C., the top of the column from about 120° to 220° C., the middle of the column from about 140° to 250° C., and the bottom of the column from about 160° to 320° C. After leaving the spinning column, the continuous filamentary materials are taken up, for example, at a speed within the range of about 50 to 350 meters or more per minute. If the continuous filamentary materials are to be washed while wound on bobbins, the resulting "as-spun" materials may be subjected to a slight steam drawing treatment at a draw ratio of from about 1.05:1 to 1.5:1 in order to prevent the fibers from relaxing and falling off the bobbin during the subsequent washing step. Further details with respect to a method for dry-spinning a continuous length of a polybenzimidazole fibrous material are shown in U.S. Pat. No. 3,502,576 to Bohrer et al which is assigned to the same assignee as the present invention and is herein incorporated by reference.

Residual spinning solvent is next removed from the continuous length of polybenzimidazole fibrous material so that the fibrous material contains less than about 1% by weight solvent based on the weight of the continuous filamentary material, and preferably so as to obtain an essentially spinning solvent-free fibrous material (i.e., a fibrous material containing less than about 0.1% solvent by weight). Typically, a simple water wash is employed; however, other solvent removal techniques or other wash materials such as acetone, methanol, methylethyl ketone and similar solvent-miscible and volatile organic solvents may be used in place of or in combination with the water. The washing operation may be conducted by collecting the polybenzimidazole fibrous material on perforated rolls or bobbins, immersing the rolls in the liquid wash bath and pressure washing the fibrous material, for example, for about 2 to 48 hours or more. Alternatively, the continuous length of polybenzimidazole fibrous material may be washed on a continuous basis by passing the fibrous material in the direction of its length through one or more liquid wash baths (e.g., for 1 to 10 minutes). A particularly preferred wash technique is disclosed in commonly assigned U.S. Pat. No. 3,743,479. Any solvent removal technique known to those skilled in the art may be selected.

The continuous length of polybenzimidazole fibrous material may next be dried to remove the major proportion of the water wash bath and/or moisture otherwise in association therein by any convenient technique. For instance, the drying operation for bobbins of yarn may be conducted at a temperature of about 150° to 300° C. for about 2 to 100 hours or more. Alternatively, the continuous length of polybenzimidazole fibrous material may be dried on a continuous basis by passing the fibrous material in the direction of its length through an appropriate drying zone (e.g., suspended in an oven provided at 300° to 400° C. for more than one minute, as above these limits degradation of fiber may occur. It is unnecessary to remove the final minor quantity of moisture from the fibrous material which has proven to be the most difficult to remove. Also, the rapid absorption of a minor quantity of moisture from the atmosphere following drying can be effectively tolerated without deleterious results.

Multifilament yarns selected for use in the process preferably contain about 10 to 500 filaments, and most preferably about 10 to 200 filaments. A multifilament tow selected for use in the process preferably contains about 1,000 to 300,000 filaments, or more, and most preferably about 50,000 to 150,000 filaments. When tows containing an extremely large number of filaments are drawn in accordance with the present invention, it is preferred that the tows be supplied to the drawing zone (described hereafter) while in a flattened ribbon-like configuration.

The continuous length of the polybenzimidazole fibrous material may be drawn through the application of a longitudinal tension. Preferably the polybenzimidazole is hot drawn at a ratio of about 2:1 to 5:1 in order to enhance its orientation. Representative drawing procedures are disclosed in commonly assigned U.S. Pat. Nos. 3,883,718, 3,836,621, 3,849,529, 3,851,025, and 3,622,660, which are hereby incorporated by reference. The polybenzimidazole fibrous material subsequent to drawing preferably possesses a denier per filament of about 1 to 30.

The above mentioned fibrous material may be arranged in a variety of configurations in its final form. It may be continuous or cut into short lengths. It is preferred to use the fibrous material to construct screens, webs, cloths, or even hollow tubular filaments which in turn provide the support for the rhodium complex.

Preparation of Fiber Catalyst

The rhodium carbonyl chloride complex $[Rh(CO)_2Cl]_2$ is most easily obtained by passing carbon monoxide over hydrated $RhCl_3$ at about 100° C., when it sublimes as red needles. This complex is well known to those skilled in the art and may be prepared in a number of other ways. The rhodium carbonyl complex then reacts with the polybenzimidazole fiber to form a precursor which is then converted to the actual catalyst according to the following illustration:

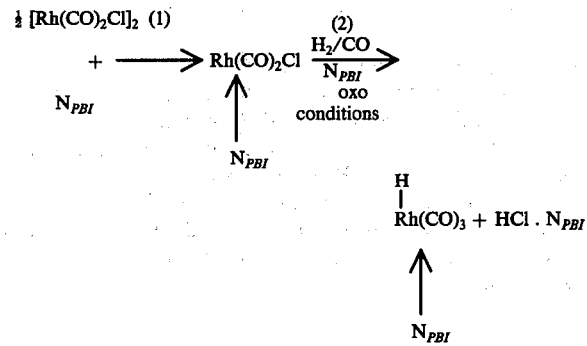

where "$N_{PBI}$" is the binding site at one of the N atoms in the benzimidazole moity which holds the Rh complex on the polymer.

The first reaction illustrates the catalyst precursor preparation and yields a product which may be generally represented as

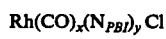

where $x + y = 3$.

The second reaction illustrates the formation, under hydroformylation conditions, of the active catalyst and yields a reaction product which may be generally represented as

where $x + y = 4$.

It is the active catalyst formed by reaction 2 which is recycled.

Although reference is made to

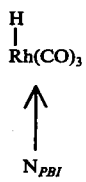

as the "actual" catalyst, even this structure may in a sense be regarded as a catalyst precursor since it is believed to exist in solution in a rapid equilibrium with coordinately less saturated species; for example

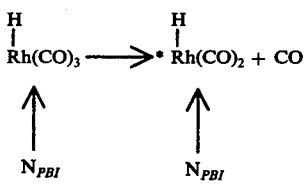

Studies of the mechanism of hydroformylation usually suggest that coordinately unsaturated species, such as *, initiate the catalysis by coordinating with the olefin to be hydroformylated. In a sense then the coordinately unsaturated structure may also be regarded as the "active" catalyst.

The principle catalyst forming reaction is a bridge splitting reaction and is illustrated by the following:

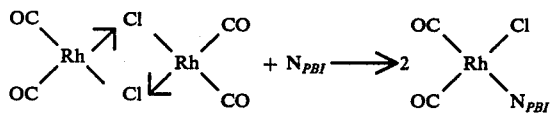

where $N_{PBI}$ is the same as above.

The method for combining the Rh with the polybenzimidazole fiber may be varied. For instance, an alternate approach such as that discussed in - J.C.S. Chem. Comm. 158 (1967) by B. R. James and G. L. Rempel, may be utilized with polybenzimidazole fibers to form the supported catalyst of the present invention.

Although [Rh (CO)$_2$Cl]$_2$ is a preferred embodiment, the formula,

where $a = -2$ when $n = 1$ and $y = 2$; $a = 0$ when $n = 2$ and $y = 1$; and X is a member selected from the group consisting essentially of Cl, Br, I, carboxylate, nitrate, thiocyanate, and sulfate, represents other rhodium carbonyls that may be utilized in the practice of this invention.

The halogens exist as "bridged" dimers having the structure

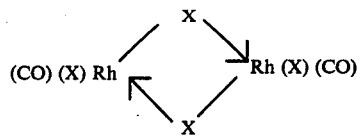

as do the carboxylate, nitrate, thiocynate and sulfate which are, for example, illustrated by the formula for the carboxylate:

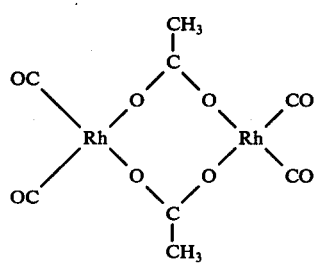

The degassed polybenzimidazole fibers are mixed in a suitable solvent which contains the rhodium carbonyl complex to form the fiber catalyst. The concentration of the polybenzimidazole fiber by weight of the solvent may vary from about 0.001% to about 100%, preferably from about 0.1% to about 50%, most preferably from about 0.5% to about 10%. The concentration of the rhodium carbonyl complex is dictated and controlled by the concentration of the rhodium metal which in turn is dictated and controlled by economics in view of the high cost of rhodium metal and rhodium compounds. Thus the molar concentration of the rhodium metal may vary from about $1 \times 10^{-6}$ M. to about 1 M., preferably from about $1 \times 10^{-5}$ M. to about $1 \times 10^{-1}$ M. and most preferably from about $1 \times 10^{-4}$ M. to about $1 \times 10^{-2}$ M. Observations generally indicate that optimum results are obtained by employing a catalyst concentration falling within the aforedefined preferred range.

Normally liquid organic solvents which are inert or which do not interfer to any substantial degree with the formation of the fiber catalyst under the operative conditions are employed. Illustrative of such solvents include the saturated hydrocarbons, such as the pentanes, naphtha, kerosene, mineral oil, cyclohexane, etc., as well as the aromatic hydrocarbons, ethers, ketones, and nitriles as illustrated by benzene, xylene, toluene, diethyl ether, acetophenone, cyclohexanone, benzonitrile and the like. Preferably benzene is used.

The resulting mixture of polybenzimidazole fibers and rhodium carbonyl complex is maintained under a pressure of from about 1 psi to about 50,000 psi, preferably from about 14.7 psi to about 6,000 psi, most preferably from about 100 psi to about 3,000 psi of a 1:1 H$_2$/CO gas mixture at a temperature of from about 0° C. to about 300° C., preferably from about 25° C. to about 200° C., most preferably from about 80° C. to about 150° C. Such pressure and temperature is maintained for a period of about 0.01 hours to about 100 hours, preferably from about 0.1 hours to about 10 hours, most preferably from about 0.5 hours to about 2 hours. The mixture is then cooled and the reaction product and solvent are separated from the fiber catalyst by filtration.

Use of the Fiber Catalyst in Hydroformylation Reactions

The fiber catalyst is employed in a hydroformylation reaction by adding the fiber catalyst in amounts of from about 0.1% to about 100% by weight of solvent, to a suitable solvent. Thus the solvent can be omitted entirely in cases where the reactant olefin is a liquid with adequate solvent properties for the $H_2$ and CO co-reactants, and for the reaction products. Normally liquid organic solvents which are inert or which do not interfere to any substantial degree with hydroformylation reactions under the operative conditions are employed. Illustrative of such solvents include those solvents mentioned above. Particularly preferred solvents for use duing the hydroformylation reaction are benzene, ethers such as glyme, diglyme, tetrahydrofuran (THF), and esters. Alcoholic solvents should be avoided because alcohols can undergo acetal and hemiacetal forming reactions with the aldehyde oxo products.

Pressure is maintained from about 1 psi to about 50,000 psi, preferably from about 14.7 psi to about 6,000 psi, most preferably from about 100 psi to about 3,500 psi under an atmosphere of a 1:1 $H_2$/CO and the mixtures heated to a temperature of from about 20° C. to about 200° C., preferably from about 80° C. to about 150° C.

A preferred industrial application of this process would include the use of screens of P.B.I. Thus, the P.B.I. screens, to which the Rh complex had been attached, can be mounted in a tubular reactor. Liquid olefin or a solution of olefin in a suitable solvent is pumped over the catalyst screens at an optimum liquid hourly space velocity (L.H.S.V.) (units of Hr $^{-1}$) together with the synthesis gas (1:1 $H_2$/CO, or 2:1 $H_2$/CO, etc.). Gases are fed at an optimum gas hourly space velocity (G.H.S.V.) (in units of hr $^{-1}$). The resultant aldehydes or alcohols are pumped out the other end of the tube free of the catalyst which is fixed in the reactors.

This process is generally applicable to the hydroformylation of any aliphatic or cycloaliphatic compound having at least one ethylenic or olefinic carbon-to-carbon bond. Moreover, one can employ a sole olefinic compound or a mixture of olefinic compounds as reactant(s). Olefins such as ethylene, propylene, the butylenes, oxygenated olefins such as allyl alcohol, the pentylenes, the hexylenes, the octylenes, the dodecylenes, the octadecylenes, 1,7-octadiene, and higher molecular weight materials, represent illustrations of suitable olefinic feeds. Suitable hydrocarbons include both branched-and straight-chain compounds having one or more carbon-to-carbon ethylenic or olefinic sites, especially those which contain from 2 to 20 carbon atoms. Many multifunctional olefins such as styrene, acrylic acid, acrylonitrile, etc. can be hydroformylated. In the case of polyolefins, it is possible to hydroformylate only one of the olefinic sites or several or all of these sites. The unsaturated carbon-to-carbon olefinic bond may be terminal, i.e., between the alpha- and beta-carbon atoms as in 1-butene, or it may be internal as illustrated by 3-hexene.

The hydrocarbon alicyclic reactants include the monocyclic and polycyclic compounds which have at least one olefinic carbon-to-carbon bond, desirably those which contain up to 20 carbon atoms. This group can be adequately illustrated by cyclopentene, cyclohexene, cycloheptene, the methylcyclohexenes, the terpenes; 4-vinylcyclohexene, dicyclopentadiene.

This invention will be further illustrated by the following examples. However, no limitation, other than those incorporated in the appended claims, are to be employed.

EXAMPLE I

The fiber catalyst was formed by mixing 2.28 g of degassed polybenzimidazole fibers in 1/2 inch lengths with 0.03 g of $[Rh(CO)_2Cl]_2$ and 100 cc of benzene. The mixture was then maintained at 120° C. for 2 hours at 2000 psi under an atmosphere of a 1:1 $H_2$/CO gas mixture. The fiber catalyst was then added to a 300 cc autoclave reactor containing 10 g of allyl alcohol in 100 cc of benzene. This mixture was pressured under 1000 psi by 1:1 $H_2$/CO gaseous mixture and heated to 120° C. for about 1 hour. The conversion of allyl alcohol to products was evident by a rapid gas absorption. Gas chromatographic analysis of the product mixture indicated that the allyl alcohol was completely converted to products. The major products were iso-butyraldehyde (approximately 84%) and alpha-hydroxy butyraldehyde (approximately 16%).

EXAMPLE II

The fiber catalyst was used two more times by filtering the benzene product solution from the fiber catalyst and adding 10 g charges of allyl alcohol in 100 cc of benzene. Under similar reaction conditions, the second and third use of the fiber catalyst resulted in rapid complete conversion of the allyl alcohol. The major products were 70% and 63% isobutraldehyde and 30% and 37% alpha-hydroxy butyraldehyde respectively.

Comparative Example

To demonstrate that $[Rh(CO)_2Cl]_2$ is not an active catalyst in the absence of polybenzimidazole fibers the hydroformylation reaction disclosed in Example I was run in the absence of polybenzimidazole fibers. No gas absorption nor conversion of allyl alcohol occurred.

What is claimed is:

1. In a hydroformylation process in which an olefin of from 2 to 20 carbon atoms is reacted with carbon monoxide and hydrogen under hydroformylation conditions wherein the temperature varies from about 20° to about 200° C and the pressure varies from about 1 to about 50,000 psi to yield a product selected from the group consisting of aldehyde, alcohol and mixtures thereof; the improvement comprising carrying out the reaction in the presence of an insolubilized polybenzimidazole fiber supported rhodium catalyst wherein a rhodium carbonyl complex of the type $[Rh(CO)_nX_y]_2{}^a$, where a may vary from 0 to $-2$, $n$ may vary from 1 to 2, $y$ may vary from 1 to 2, and X is a member selected from the group consisting essentially of a halogen, carboxylate, nitrate, thiocyanate and sulfate, forms a polybenzimidazole complex with the benzimidazole units of the polybenzimidazole fiber surface, said benzimidazole units acting as donor ligands for the rhodium carbonyl complex.

2. The process of claim 1 wherein said polybenzimidazole fibrous material consists essentially of recurring units of the formula:

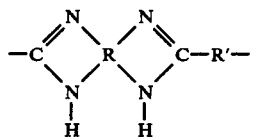

wherein R is a tetravalent aromatic nucleus, with the nitrogen atoms forming the benzimidazole rings paired upon adjacent carbon atoms of said aromatic nucleus, and R' is selected from the group consisting of (1) an aromatic ring, (2) an alkylene group having from 4 to 8 carbon atoms and (3) a heterocyclic ring selected from the group consisting of (a) pyridine, (b) pyrazone, (c) furan, (d) quinoline, (e) thiophene, and (f) pyran.

3. The process of claim 1 wherein said polybenzimidazole fibrous material is poly-2,2'-(m-phenylene)-5,5'-bibenzimidazole.

4. The process of claim 1 wherein $a = 0$, $n = 2$, $y = 1$, and x = chlorine in said rhodium carbonyl complex.

* * * * *